(12) United States Patent
Sun et al.

(10) Patent No.: US 10,648,039 B2
(45) Date of Patent: May 12, 2020

(54) USE OF METHYLATION SITES IN Y CHROMOSOME AS PROSTATE CANCER DIAGNOSIS MARKER

(71) Applicant: WUXI SHENRUI BIO-PHARMACEUTICALS CO., LTD., Huishan District, Wuxi, Jiangsu (CN)

(72) Inventors: Yingli Sun, Beijing (CN); Lushuai Yao, Beijing (CN)

(73) Assignee: WUXI SHENRUI BIO-PHARMACEUTICALS CO., LTD., Wuxi, Jiangsu (CN)

( * ) Notice: Subject to any disclaimer, the term of this patent is extended or adjusted under 35 U.S.C. 154(b) by 139 days.

(21) Appl. No.: 15/544,735

(22) PCT Filed: Dec. 30, 2015

(86) PCT No.: PCT/CN2015/099922
§ 371 (c)(1),
(2) Date: Jul. 19, 2017

(87) PCT Pub. No.: WO2016/115967
PCT Pub. Date: Jul. 28, 2016

(65) Prior Publication Data
US 2017/0362663 A1    Dec. 21, 2017

(30) Foreign Application Priority Data
Jan. 20, 2015  (CN) .......................... 2015 1 0027708

(51) Int. Cl.
C12Q 1/68      (2018.01)
C12Q 1/6886    (2018.01)
C12Q 1/6809    (2018.01)
C12Q 1/6872    (2018.01)

(52) U.S. Cl.
CPC ......... *C12Q 1/6886* (2013.01); *C12Q 1/6809* (2013.01); *C12Q 1/6872* (2013.01); *C12Q 2600/106* (2013.01); *C12Q 2600/118* (2013.01); *C12Q 2600/154* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

2014/0315192 A1   10/2014   Wang et al.

FOREIGN PATENT DOCUMENTS

| CN | 101220392 A | 7/2008 |
|---|---|---|
| CN | 101724685 A | 6/2010 |
| WO | 2014/160829 A2 | 10/2014 |

OTHER PUBLICATIONS

Slieker et al. (Epigenetics & Chromatin, 2013 6:26, 12 pages) (Year: 2013).*
Yegnasubrannanian et al. BMC Genomics 2011, 12:313, 19 pages (Year: 2011).*
Kristensen et al. Clinical Chemistry 55:8, pp. 1471-1483 (2009) (Year: 2009).*
Yao et al. (Oncotarget, vol. 6, No. 38, pp. 40611-40621; Published Oct. 16, 2015) (Year: 2015).*
Kim et al. (Kim JW et al. (2012) Identification of New Differentially Methylated Genes That Have Potential Functional Consequences in Prostate Cancer. PLoS ONE 7(10): e48455. doi:10.1371/journal.pone.0048455. (Year: 2012).*
Bibikova et al. (Genomics 98 (2011) 288-295) (Year: 2011).*
Barker et al.( Genome Res. 2004 14: 901-907) (Year: 2004).*
Patra, A., et al., "5-Aza-2'-deoxycytidine stress response and apoptosis in prostate cancer" Clin. Epigenetics (2011) 2(2):339-48.
Slieker, R.C., et al., "Identification and systematic annotation of tissue-specific differentially methylated regions using the Illumina 450k array" Epigenetics Chromatin (2013) 6(1):26.
Illumina, "Infinium® HumanMethylation450 BeadChip: Product Information" San Diego, CA (2011).
Yegnasubramanian, S., et al., "Chromosome-wide mapping of DNA methylation patterns in normal and malignant prostate cells reveals pervasive methylation of gene-associated and conserved intergenic sequences" BMC Genomics (2011) 12:313.
Khosravi, P., et al., "Analysis of Candidate Genes has proposed the Role of Y Chromosome in Human Prostate Cancer" Iran J. Cancer Prev. (2014) 7(4):204-11.
Yao, L., et al., "Identification of specific DNA methylation sites on the Y-chromosome as biomarker in prostate cancer" Oncotarget (2015) 6(38):40611-21.
Liu, Zhi-Jian et al., "Epigenetics and Cancer: Target Epigenetic Alterations in Tumor", Chinese Journal of Biochemistry and Molecular Biology, 27(4): 310-315 (2011) [English Abstract attached].
International Search Report, dated Mar. 14, 2016, issued in corresponding International Application No. PCT/CN2015/099922.

* cited by examiner

*Primary Examiner* — Juliet C Switzer
(74) *Attorney, Agent, or Firm* — Robert C. Netter, Jr.; Dann, Dorfman, Herrell & Skillman

(57) ABSTRACT

Disclosed is a use of methylation sites as a disease diagnosis marker, in particular relating to a use of methylation sites in a Y chromosome as a prostate cancer diagnosis marker. More particularly, the method and criterion for screening methylation sites in chromosomes associated with a disease are established in the present invention, and using prostate cancer as an example, six methylation sites in the Y chromosome associated with the prostate cancer diagnosis are screened out. Methylation sites in the Y chromosome screened can be used for early and rapid diagnosis of the disease as a prostate cancer diagnosis marker.

5 Claims, 7 Drawing Sheets
Specification includes a Sequence Listing.

USE OF METHYLATION SITES IN Y CHROMOSOME AS PROSTATE CANCER DIAGNOSIS MARKER

CROSS-REFERENCE TO RELATED APPLICATIONS

This application is a § 371 of International Application No. PCT/CN2015/099922, filed Dec. 30, 2015, which claims priority from Chinese Patent Application CN201510027708.0, filed Jan. 20, 2015. The entire disclosure of each of the aforesaid applications is incorporated by reference in the present application.

TECHNICAL FIELD

The present disclosure relates to a use of a methylation site as a disease diagnosis marker, in particular relates to a use of a methylation site in a Y chromosome as a prostate cancer diagnosis marker.

BACKGROUND

DNA methylation is a common epigenetic modification. Under the catalysis of DNA methyltransferase, the carbon atom at the 5th position of cytosine is methylated using the methyl group provided by S-adenosylmethionine, thereby transforming cytosine to 5-methylcytosine, which plays a vital role in the regulation of gene expression.

Cancer, also known as malignant tumor, is a disease caused by the abnormalities in the control of cell growth and proliferation mechanisms. Under normal circumstances, the growth and proliferation of cells are strictly regulated by some genes regulating the growth and development, including the oncogenes and the cancer suppressor genes, to maintain a normal physiological state; when affected by multiple factors such as radiation, chemical contamination, viral infection and endocrine imbalance, the activation of oncogenes and inactivation of tumor suppressor genes in vivo will be caused, thereby leading to the occurrence of cancer. In addition to the gene mutations, abnormal regulations of the epigenetics such as histone modification, DNA methylation also play an important role during the occurrence and development of tumor, the abnormalities of epigenetic modification can be found in a variety of cancers. In short, the occurrence of tumor is an extremely complex process, it is the result of abnormal regulation and its accumulation occurred in oncogenes, cancer suppressor genes and epigenetic modification in vivo.

DNA methylation has a close relation with the occurrence of cancer, the abnormalities of DNA methylation have been found in many cancers. DNA methylation has a certain degree of stability, it is an early event during the occurrence of cancer. In recent years, many studies have shown that abnormalities of DNA methylation can be used as a biomarker for cancer diagnosis. At present, abnormalities of DNA methylation in many specific gene promoter regions are used as a potential marker for the diagnosis for prostate cancer.

At present, the main diagnostic methods for prostate cancer are rectal diagnosis, serum PSA examination, and tissue immune biopsy, etc., in which the tissue immune biopsy is the gold diagnostic method for prostate cancer. However, since it is required to take the prostate tissue from a patient firstly, which will bring about great pains for the patient, it is not suitable for the previous diagnosis. PSA is currently used as a marker for the previous diagnosis for prostate cancer, but it is not quite accurate in terms of examination, and a certain gray zone exists. Therefore, it is very urgent to find a convenient and accurate diagnosis marker for the early diagnosis for prostate cancer.

Meanwhile, there are various methods for monitoring the DNA methylation in the prior art, for example, a quantitative analysis method for monitoring the DNA methylation disclosed in CN 104062334A, as another example, a DNA methylation chip technology. However, at the present stage, there exists a lack of a unified and more accurate criterion when determining whether the methylation is abnormal, therefore it is unable to predict the risk for cancer as early as possible through the change of the methylation level at specific sites.

SUMMARY OF THE DISCLOSURE

The inventors of the present disclosure have established a unified, standard method for screening a disease-related methylation site and screened out a methylation site in a Y chromosome associated with prostate cancer, whereby completing the present disclosure.

The first aspect of the present disclosure relates to a use of a reagent for detecting a methylation level of a methylation site in a Y chromosome of a sample to be tested of a subject in the preparation of a kit, the kit is used for one or more application(s) selected from the group consisting of: diagnosis for prostate cancer, assessment of a risk for prostate cancer, evaluation of a therapeutic effect on prostate cancer, and screening of a therapeutic drug for prostate cancer; the methylation site in a Y chromosome is one or more selected from the group consisting of cg03052502, cg04462340, cg05163709, cg05544622, cg14466580 and cg27539833.

In some embodiments, the sample to be tested is selected from the group consisting of tissue, urine (e.g., urine after prostate massage) and prostatic fluid.

In some embodiments, the sample to be tested is selected from the group consisting of urine (e.g., urine after prostate massage) and prostatic fluid.

In some embodiments, the methylation site in a Y chromosome is selected from the group consisting of cg05163709 and cg27539833.

In some embodiments, the method for detecting a methylation level of a methylation site in a Y chromosome of a sample to be tested of a subject is selected from the group consisting of pyrosequencing, bisulfite sequencing, quantitative and/or qualitative methylation-specific polymerase chain reaction, southern blotting, restriction landmark genomic scanning, single nucleotide primer extension, CpG island microarray, single nucleotide primer extension (SN-UPE), combined sodium bisulfite restriction endonuclease analysis and mass spectrometry.

In some embodiments, the reagent is an oligonucleotide primer which is used for amplifying a nucleotide sequence comprising a methylation site in a Y chromosome.

The second aspect of the present disclosure relates to a kit comprising a reagent for detecting a methylation level of a methylation site in a Y chromosome of a sample to be tested of a subject, the kit is used for one or more application(s) selected from the group consisting of: diagnosis for prostate cancer, assessment of a risk for prostate cancer, evaluation of a therapeutic effect on prostate cancer, and screening of a therapeutic drug for prostate cancer; the methylation site in a Y chromosome is one or more selected from the group consisting of cg03052502, cg04462340, cg05163709, cg05544622, cg14466580 and cg27539833.

In some embodiments, the sample to be tested is selected from the group consisting of tissue, urine (e.g., urine after prostate massage) and prostatic fluid.

In some embodiments, the sample to be tested is selected from the group consisting of urine (e.g., urine after prostate massage) and prostatic fluid.

In some embodiments, the methylation site in a Y chromosome is selected from the group consisting of cg05163709 and cg27539833.

In some embodiments, the method for detecting a methylation level of a methylation site in a Y chromosome of a sample to be tested of a subject is selected from the group consisting of pyrosequencing, bisulfite sequencing, quantitative and/or qualitative methylation-specific polymerase chain reaction, southern blotting, restriction landmark genomic scanning, single nucleotide primer extension, CpG island microarray, single nucleotide primer extension (SN-UPE), combined sodium bisulfite restriction endonuclease analysis and mass spectrometry.

In some embodiments, the reagent is an oligonucleotide primer which is used for amplifying a nucleotide sequence comprising a methylation site in a Y chromosome.

The third aspect of the present disclosure relates to a method for diagnosis for prostate cancer, assessment of a risk for prostate cancer, evaluation of a therapeutic effect on prostate cancer, and screening of a drug for prostate cancer, the method comprises a step of detecting a methylation level of a methylation site in a Y chromosome of a sample to be tested of a subject; the methylation site in a Y chromosome is one or more selected from the group consisting of cg03052502, cg04462340, cg05163709, cg05544622, cg14466580 and cg27539833.

In some embodiments, when the methylation level of the methylation site selected from one or more of cg03052502, cg04462340, cg05544622, cg14466580 and cg27539833 is decreased as compared to a normal sample or a normal reference value, it is indicated that the subject has suffered from prostate cancer or a high risk for prostate cancer; when the methylation level of the methylation site of cg05163709 is increased as compared to a normal sample or a normal reference value, it is indicated that the subject has suffered from prostate cancer or a high risk for prostate cancer.

In some embodiments, when the methylation level of the methylation site selected from one or more of cg03052502, cg04462340, cg05544622, cg14466580 and cg27539833 is increased as compared to that prior to treatment or use of a drug for screening, it is indicated that the treatment for the subject is effective or the drug for screening is effective; when the methylation level of the methylation site of cg05163709 is decreased as compared to that prior to treatment or use of a drug for screening, it is indicated that the treatment for the subject is effective or the drug for screening is effective.

In some embodiments, the sample to be tested is selected from the group consisting of tissue, urine (e.g., urine after prostate massage) and prostatic fluid.

In some embodiments, the sample to be tested is selected from the group consisting of urine (e.g., urine after prostate massage) and prostatic fluid.

In some embodiments, the methylation site in a Y chromosome is selected from the group consisting of cg05163709 and cg27539833.

In some embodiments, the method for detecting a methylation level of a methylation site in a Y chromosome of a sample to be tested of a subject is selected from the group consisting of pyrosequencing, bisulfite sequencing, quantitative and/or qualitative methylation-specific polymerase chain reaction, southern blotting, restriction landmark genomic scanning, single nucleotide primer extension, CpG island microarray, single nucleotide primer extension (SN-UPE), combined sodium bisulfite restriction endonuclease analysis and mass spectrometry.

In some embodiments, the method for detecting a methylation level of a methylation site in a Y chromosome of a sample to be tested of a subject comprises a step of using an oligonucleotide primer which is used for amplifying a nucleotide sequence comprising a methylation site in a Y chromosome.

The fourth aspect of the present disclosure relates to the use of a methylation site in a Y chromosome as a biomarker for diagnosis for prostate cancer, assessment of a risk for prostate cancer, evaluation of a therapeutic effect on prostate cancer, an screening of a drug for prostate cancer, the methylation site in a Y chromosome is one or more selected from the group consisting of cg03052502, cg04462340, cg05163709, cg05544622, cg14466580 and cg27539833.

In some embodiments, the diagnosis for prostate cancer, the assessment of the risk for prostate cancer, the evaluation of the therapeutic effect on prostate cancer, and the screening of the drug for treating prostate cancer can be performed by detecting the methylation level of the methylation site in a Y chromosome.

The fifth aspect of the present disclosure relates to a biomarker for diagnosis for prostate cancer, assessment of a risk for prostate cancer, evaluation of a therapeutic effect on prostate cancer, and screening of a drug for prostate cancer, the biomarker is a methylation site in a Y chromosome which is one or more selected from the group consisting of cg03052502, cg04462340, cg05163709, cg05544622, cg14466580 and cg27539833.

In some embodiments, the diagnosis for prostate cancer, the assessment of the risk for prostate cancer, the evaluation of the therapeutic effect on prostate cancer, and the screening of the drug for treating prostate cancer can be performed by detecting the methylation level of the methylation site in a Y chromosome.

The sixth aspect of the present disclosure relates to a method for screening the methylation site in a Y chromosome associated with a disease, the method comprises: 1) obtaining the patient's disease sample and normal sample; 2) determining the information of methylation of the chromosome in the disease sample and the normal sample; 3) screening the methylation conserved site according to the information of methylation of the chromosome in the normal sample; 4) screening the methylation site in the disease sample having obvious differences from that in the normal sample according to the information of methylation of the chromosome in the disease sample and the normal sample; 5) combining the results from steps 3) and 4) to obtain the methylation conserved site having obvious differences which is the methylation site in the chromosome associated with the disease.

In some embodiments, the disease is a cancer, for example prostate cancer.

In some embodiments, the chromosome is a euchromosome or a sex chromosome (e.g., a Y chromosome).

In some embodiments, the sample is derived from tissue (e.g., cancerous tissue), blood, urine, feces or tissue fluid (e.g., prostatic fluid).

In some embodiments, the methylation conserved site refers to a methylation site having a methylation level with a standard deviation SD value of less than or equal to 0.25 in the normal sample.

In some embodiments, the methylation site having obvious differences is a site at which the change in the methylation level is 0.2 or more and the p value and the q value are both less than or equal to 0.01 when the disease sample is compared with the normal sample; the change is an increase or a decrease.

The present disclosure also relates to a method for diagnosis for prostate cancer, the method comprises a step of screening a methylation site in a Y chromosome associated with prostate cancer.

In some embodiments, the steps for screening the methylation site in a Y chromosome associated with prostate cancer comprise: 1) obtaining the disease sample and normal sample from the patient with prostate cancer; 2) determining the information of methylation of the Y chromosome in the disease sample and the normal sample; 3) screening the methylation conserved sites according to the information of methylation of the Y chromosome in the normal sample; 4) screening the methylation site in the disease sample having obvious differences from that in the normal sample according to the information of methylation of the Y chromosome in the disease sample and the normal sample; 5) combining the results from steps 3) and 4) to obtain the methylation conserved site having obvious differences which is the methylation site in the chromosome associated with prostate cancer.

In some embodiments, the sample is derived from tissue (e.g., cancerous tissue), blood, urine (e.g., urine after prostate massage), feces or tissue fluid (e.g., prostatic fluid).

In some embodiments, the methylation conserved site refers to a methylation site having a methylation level with a standard deviation SD value of less than or equal to 0.25 in the normal sample.

In some embodiments, the methylation site having obvious differences is a site at which the change in the methylation level is 0.2 or more and the p value and the q value are both less than or equal to 0.01 when the disease sample is compared with the normal sample; the change is an increase or a decrease.

In the present disclosure, the "diagnosis", "assessment of a risk for a disease" and "evaluation of a therapeutic effect" have the meaning well-known in the art. For example, the "diagnosis" refers to a judgment on whether one suffers from the disease; the "assessment of a risk for a disease" refers to an assessment on the magnitude of a risk for suffering from a disease and the risk for recurrence after treatment; the "evaluation of a therapeutic effect" refers to an evaluation on whether there is any therapeutic effect, for example, if the symptoms are relieved, disappear, the size of focus is reduced or disappear, or the disease is no longer progressing, the treatment is effective.

In the present disclosure, the "disease sample" refers to a tissue sample in which the focus is located or a tissue sample associated with the disease, for example, a disease sample of prostate cancer includes both the cancerous tissue samples of prostate cancer and the prostatic fluid samples and urine samples associated with prostate cancer, especially urine samples after prostate massage.

In the present disclosure, the "normal sample" and the "normal specimen" have the same meaning and refer to a sample of a normal tissue opposite to the "disease sample". For example, when the disease sample is a cancerous tissue sample, the normal sample may be a paracancerous tissue sample; and when the disease sample is a diseased blood or urine sample, the normal sample may be a pre-diseased blood or urine sample.

In the present disclosure, the "normal reference value" has a meaning well-known in the art and refers to a normal value range of an index obtained on the basis of a certain number of normal samples, for example, on the basis of a certain number of normal samples, the normal reference value range for a methylation level of a methylation site in a Y chromosome can be obtained. When determining whether an index of a sample is within the normal range, this normal reference value has reference significance.

In the present disclosure, the kit may further contain one or more reagent(s) selected from the group consisting of dNTP, buffer, DNA polymerase, restriction endonuclease (including methyl-specific endonuclease), and marker (including fluorescent marker, chemiluminescent marker and radioactive marker, etc.).

In the present disclosure, the method for designing an oligonucleotide primer for detecting a methylation level of a methylation site based on the methylation site on the genome is well known in the art, and the oligonucleotide primer can be complementary to or hybridized with the nucleic acid sequence at which the methylation site is located.

In the present disclosure, the number of the oligonucleotide primer is at least one or a group of primers, for example, at least 2, at least 3, at least 4, at least 5, at least 6, at least 7, at least 8, at least 9, at least 10, at least 11 or at least 12, which are complementary to or hybridized with the nucleic acid sequence at which the methylation site is located.

In a specific embodiment of the present disclosure, the primers for amplifying the site cg05163709 are:

```
F:
                                        (SEQ ID NO: 1)
GGAAAGGGGTGATTAAATATTTAGTTA;

R:
                                        (SEQ ID NO: 2)
5'-BIOTIN-CAACCTAATAAAAAACTATACAAACACAT;

S-primer:
                                        (SEQ ID NO: 3)
ATAAGTATGTTTAATTATTGTTTAAG.
```

In a specific embodiment of the present disclosure, the primers for amplifying the site cg27539833 are:

```
F:
                                        (SEQ ID NO: 4)
GGAATAGTTTAGTTAAAGAAAAAGGTTAAGAT;

R:
                                        (SEQ ID NO: 5)
5'-BIOTIN-AATTTACCACAATACACAAAAAACTAACTACTTA;

S-primer:
                                        (SEQ ID NO: 6)
AGATTTTAGTAGTTTTTTGTCGTTA.
```

In the present disclosure, the representing method "cg" for a methylation site in a chromosome is based on the nomenclature for each methylation site by 450K chip from Illumina Corporation. The meaning of the representing method is well known in the art and the methylation site represented thereby one to one corresponds to a specific methylation site in the chromosome, and one skilled in the art can accurately and uniquely match a site represented according to this method onto a human chromosome.

In the present disclosure, the "methylation" refers to the methylation of the CpG site.

In the present disclosure, the methylation level may be represented by a method well known in the art, for example it can be represented by the ratio of methylated cytosine C detected to the total C detected at the time of sequencing, specifically β value (beta_value), and the numerical range thereof is 0-1 or 0-100%. In some embodiments, the representing method for methylation level is β value (beta_value), and the numerical range thereof is 0-1.

In the present disclosure, the method for determining the increase or decrease of the methylation level is the difference value of β values (for example, the difference value between samples) is greater than or equal to 0.2.

In the present disclosure, the "SD value", i.e. the standard deviation value, has the meaning and calculation method well known in the art, for example, one can make reference to "Biometry and Experimental Design" (Ming Daoxu, China Agriculture Press, August 2010, $4^{th}$ Edition).

In the present disclosure, "p value" and "q value" have the meanings and calculation methods well known in the art, for example one can refer to "Biometry and Experimental Design", for example p value=probability of ones assumed to be correct but rejected=number of negative ones/total number, which is an inspection probability for a sample data; q value=probability of ones rejected but correct=number of false positive ones/number of ones presumably positive, which is an inspection probability of the deduction you obtained, and is calculated based on the P value. It can be said that the q value is a further statistic of the p value.

Beneficial Effects of the Disclosure

The present disclosure has established a method and criterion for screening a methylation site in a chromosome associated with a disease, it also screens out six methylation sites in the Y chromosome associated with the prostate cancer diagnosis by using prostate cancer as an example. The screened methylation sites in the Y chromosome can be used for early and rapid diagnosis for the disease as a prostate cancer diagnosis marker.

DETAILED DESCRIPTION

Although the embodiments of the present disclosure will be described in detail with reference to the following examples, it will be understood by those skilled in the art that the following examples are merely intended to be illustrative of the present disclosure and are not to be construed as limiting the scope of the present disclosure. The Examples in which the specific conditions are not specified are carried out according to the conventional conditions or conditions suggested by the manufacturer. The used reagents or instruments of which the manufacturers are not indicated, are all commercially available conventional products.

Example 1 Collection and Identification of Cancerous Tissues and Paracancerous Tissues of Prostate Cancer The tissues were collected from prostate cancer patients undergoing cancer cutting operation, the cancerous tissues and paracancerous tissues were distinguished through tissue immune biopsy by an experienced physician, and collected correspondingly (the samples were provided by Shanghai Changhai Hospital).

Example 2 Screening of Conserved Methylation Sites

Figure 1:
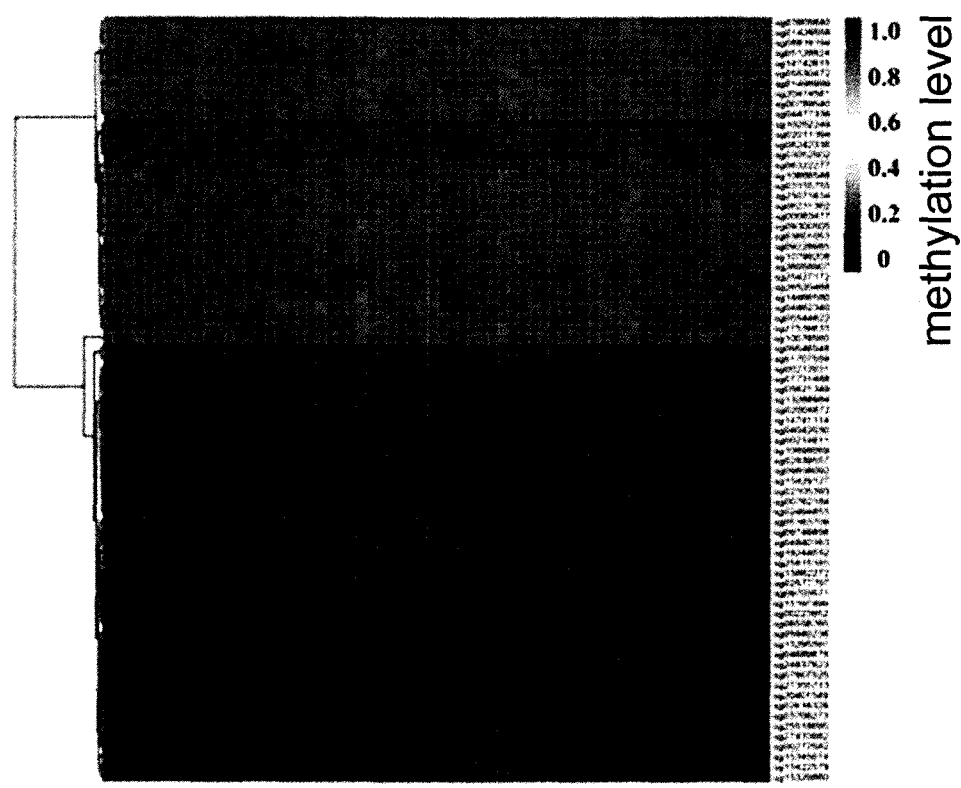
FIG. 1 shows the thermal map of the methylation level of 75 conserved sites screened out from the paracancerous tissue.

Paracancerous tissues from 66 cases of patients with prostate cancer were collected and taken, and DNAs were extracted therefrom and amplified (QIAamp DNA Mini Kit (Cat. No. 51306)). Whole genome methylation levels of 66 samples were measured using the DNA methylation chip Illumina 450K (Infinium HumanMethylation450 BeadChip array), the initial data obtained by scanning were processed through the GenomeStudio software according to Illumina's official Methylation Analysis Algorithms to generate the data containing the methylation level at each site for each sample, i.e., Raw data, then the methylation levels of sites after filtration, i.e., Norm data, were given upon the correction and normalization of deviation caused by different types of fluorescence and probe, and site filtration, and the methylation level of each site was represented with β value (0-1). The methylation information in a Y chromosome therein was taken, subjected to analysis and comparision, and 75 methylation conserved sites (SD value ≤0.25) were screened out according to the SD values of the methylation levels (β value) between samples. The results were shown in FIG. 1.

Example 3 Screening of Methylation Sites Having Obvious Differences

Figure 2:
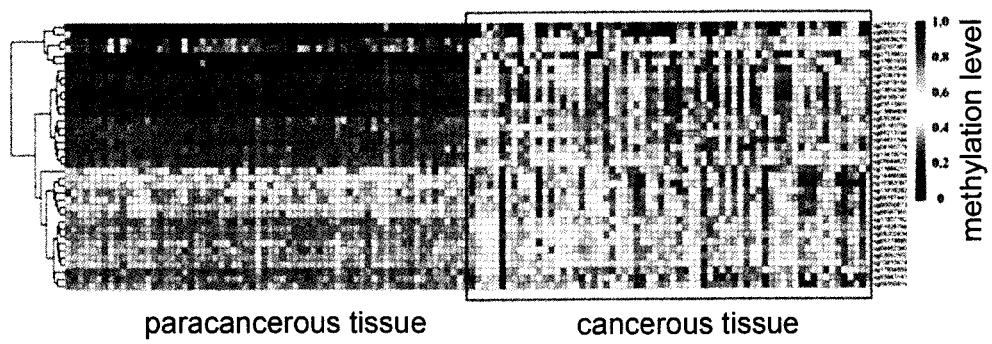
FIG. 2 shows the 37 methylation sites having significant changes screened out through the comparison of the cancer tissue with the paracancerous tissue.

37 DNA methylation sites having significant changes in the cancerous tissues were screened out, i.e., the site with a Δβ≥0.2 (i.e., the difference value of β value between the cancerous tissues and paracancerous tissues ≥0.2) and a p value ≤0.01 according to the comparison of DNA methylation levels (β value) in a Y chromosome between 66 pairs of cancerous tissues and paracancerous tissues using the Illumina Methylation Analyzer (IMA) software package, see FIG. 2.

Example 4 Screening of Conserved Sites Having Significant Changes

Figure 3:
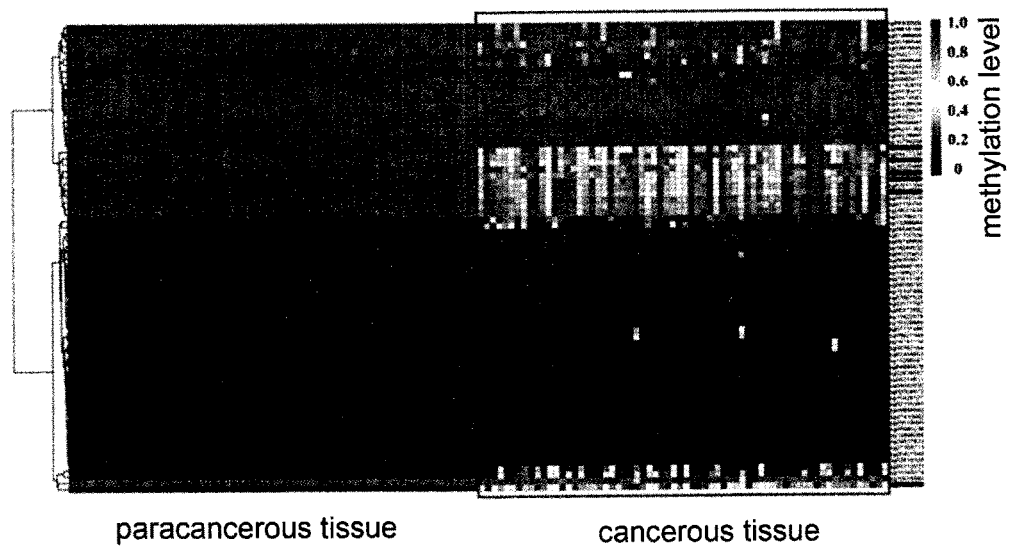
FIG. 3 and FIG. 4 show the 75 methylation sites conserved in the paracancerous tissue (FIG. 3), wherein 6 methylation sites have significant changes in the cancerous tissue (FIG. 4).
Figure 4:
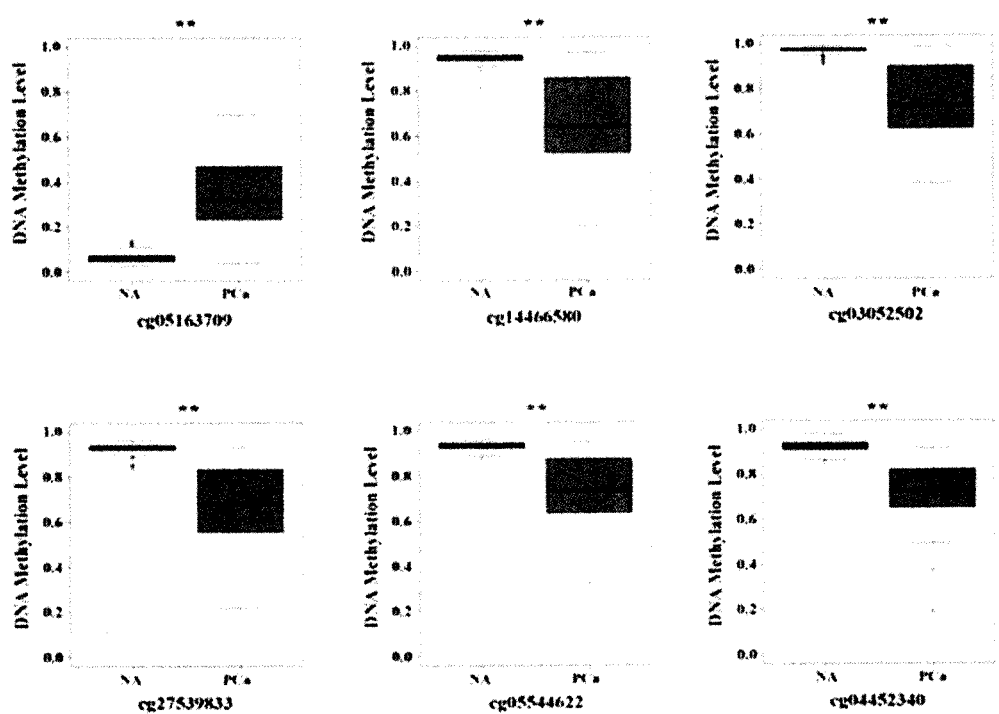

According to the results in Example 2 and Example 3, the intersections of both (i.e., the methylation sites which were conserved in the paracancerous tissues and had significant changes in the cancerous tissues) were screened out, there were a total of 6 sites of cg03052502, cg04462340, cg05163709, cg05544622, cg14466580 and cg27539833 (see FIG. 3 and FIG. 4), and the specific information of these 6 sites was as shown in Table 1.

TABLE 1

Specific information of methylation sites having significant changes in cancerous tissue

| Target ID | P-Value | Adjust Pval | Beta-Difference | Mean_PCa | Mean_NA | UCSC_REFGENE_NAME | UCSC_REFGENE_GROUP | MAPINFO |
|---|---|---|---|---|---|---|---|---|
| cg03052502 | 4.68E−20 | 4.82E−19 | −0.22197 | 0.750654 | 0.972621 | FAM197Y2 | TSS1500 | 9193029 |
| cg04462340 | 2.30E−23 | 3.65E−22 | −0.20581 | 0.718943 | 0.924757 | | | 13911503 |
| cg05163709 | 9.96E−28 | 5.42E−26 | 0.284045 | 0.345909 | 0.061864 | PRKY | TSS1500 | 7141248 |
| cg05544622 | 2.47E−19 | 1.96E−18 | −0.20167 | 0.734588 | 0.936261 | TSPY1; TSPY4 | TSS1500; Body | 9303646 |
| cg14466580 | 1.50E−20 | 1.73E−19 | −0.28341 | 0.663387 | 0.946797 | | | 10037020 |
| cg27539833 | 9.32E−23 | 1.27E−21 | −0.25101 | 0.67675 | 0.927762 | TGIF2LY | 3'UTR | 3447947 |

Figure 5:
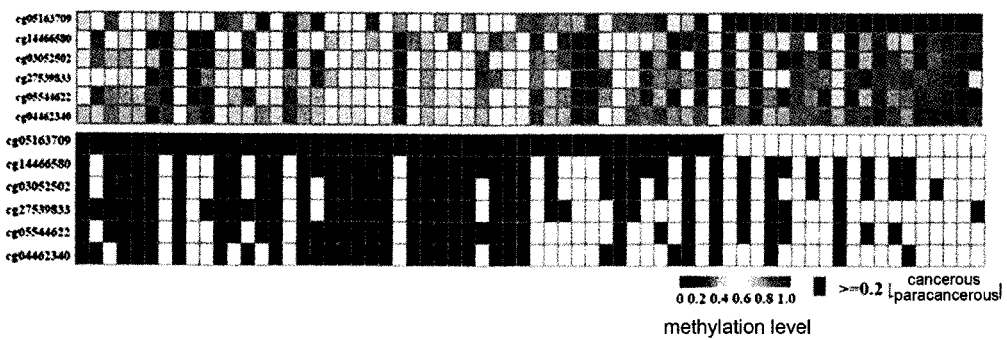
FIG. 5 shows the methylation level of the final 6 sites screened out (the Figure above), and the proportion of the occurrence of significant change of each site in 66 cancerous tissues (the Figure below, the black mark represents the significant change).
Figure 6:
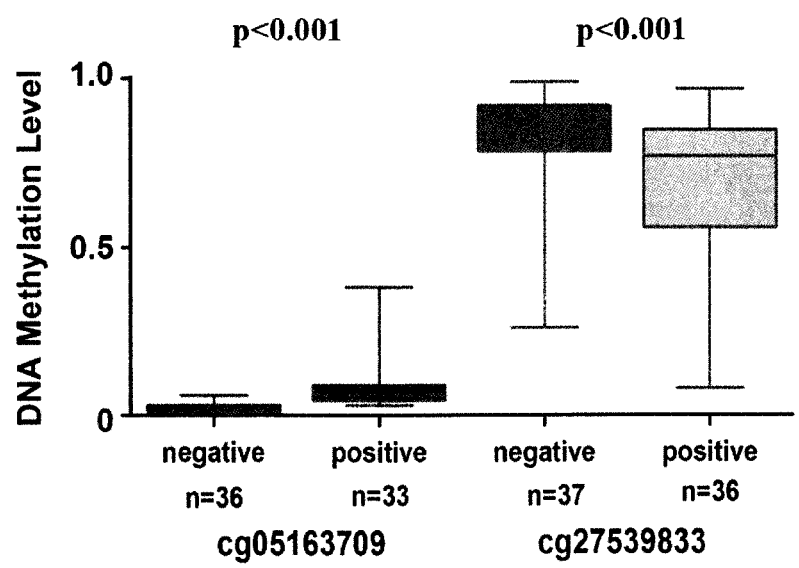
FIG. 6 shows the DNA methylation level of sites cg05163709 and cg27539833 in the positive and negative prostate puncture biopsies through the detection for a urine sample.

These 6 sites were compared and detected in each pair of cancerous tissue-paracancerous tissue to calculate the proportion of the cancerous tissue which indeed had a significant change in the methylation (see FIG. 5). These 6 intersection sites were the conserved sites having significant changes in the methylation level in the cancerous tissues and can be used as markers for the diagnosis for prostate cancer.

Figure 7:
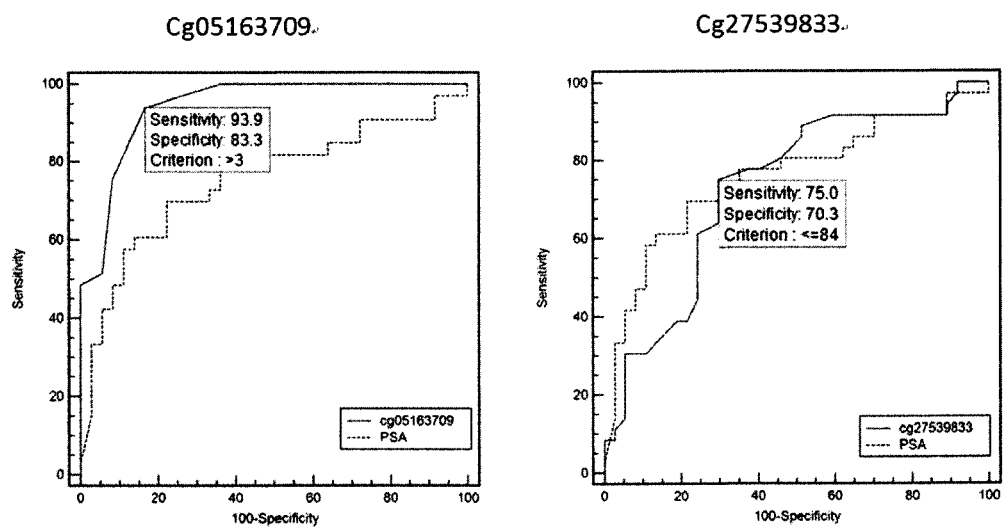
FIG. 7 shows the comparison of diagnostic efficiency between the methylation of sites cg05163709 and cg27539833 as a diagnosis marker and the PSA.

Example 5 Detection of Methylation Levels of Sites Cg05163709 and Cg27539833 in the Urine Sample The urine samples were obtained from patients with prostate cancer and normal subjects through the prostate massage, and DNAs were extracted therefrom. The methylation levels of sites cg05163709 and cg27539833 were obtained with pyrosequencing, the changes in methylation levels of these two sites in the urine samples were compared and analyzed between the negative and positive specimens from prostate puncture biopsies, as shown in FIG. 7.

The sequence of each primer is as follows:

```
cg05163709:
F:
                                              (SEQ ID NO: 1)
GGAAAGGGGTGATTAAATATTTAGTTA;

R:
                                              (SEQ ID NO: 2)
5'-BIOTIN-CAACCTAATAAAAAACTATACAAACACAT;

S-primer:
                                              (SEQ ID NO: 3)
ATAAGTATGTTTAATTATTGTTTAG.

Cg27539833
F:
                                              (SEQ ID NO: 4)
GGAATAGTTTAGTTAAAGAAAAAGGTTAAGAT;

R:
                                              (SEQ ID NO: 5)
5'-BIOTIN-AATTTACCACAATACACAAAAAACTAACTACTTA;

S-primer:
                                              (SEQ ID NO: 6)
AGATTTTAGTAGTTTTTTGTCGTTA.
```

Example 6 the Superior Diagnostic Efficiency of the Methylation of Site Cg05163709 as a Diagnosis Marker Over PSA According to the experimental results of Example 5, the diagnostic efficiencies of the methylation of sites cg05163709 and cg27539833 as diagnosis markers were analyzed by the receiver operating curve (ROC), and it was found that although the area under the curve ROC (AUC) of site cg27539833 (0.729) had no obvious advantage as compared with that of PSA (0.753), the AUC of site cg05163709 (0.944) was significantly superior to that of PSA (0.753), therefore it had higher sensitivity (93.9%) and specificity (83.3%) as a diagnosis marker of prostate cancer.

While the specific embodiments of the present disclosure have been described in detail, those skilled in the art will appreciate that according to all teachings that have been disclosed, various modifications and substitutions can be made to those details, all of which are within the protection scope of the present disclosure. The full scope of the present disclosure is given by the appended claims and any equivalents thereof

The invention claimed is:

1. A method for detecting a methylation level of a methylation site in a Y chromosome in a sample obtained from a subject, wherein the methylation site is cg05163709, said method comprising obtaining methylation levels of a test sample by pyrosequencing, wherein the pyrosequencing employs a primer pair consisting of SEQ ID NO: 1 and SEQ ID NO: 2 and a sequencing primer consisting of SEQ ID NO: 3, the method being useful for diagnosis for prostate cancer, assessment of a risk for prostate cancer, evaluation of a therapeutic effect on prostate cancer, and screening of a therapeutic drug for prostate cancer.

2. The method of claim 1, wherein the test sample is selected from the group consisting of tissue, urine and prostatic fluid said urine optionally being obtained following prostate massage.

3. The method of claim 2, wherein the test sample is selected from the group consisting of urine and prostatic fluid.

4. The method of claim 1, wherein when the methylation level of the methylation site of cg05163709 is increased as compared to a normal sample or a normal reference value, the subject has prostate cancer or is at a high risk for prostate cancer.

5. The method of claim 1, for screening of a therapeutic drug for prostate cancer, wherein a decrease of the methylation level of the methylation site of cg05163709 as compared to levels observed prior to administration of said therapeutic drug indicates that said therapeutic drug has efficacy for treatment of prostate cancer.

* * * * *

SEQUENCE LISTING

<160> NUMBER OF SEQ ID NOS: 6

<210> SEQ ID NO 1
<211> LENGTH: 27
<212> TYPE: DNA
<213> ORGANISM: Artificial sequence
<220> FEATURE:
<223> OTHER INFORMATION: primer

<400> SEQUENCE: 1
ggaaaggggt gattaaatat ttagtta                                      27

<210> SEQ ID NO 2
<211> LENGTH: 29
<212> TYPE: DNA

```
<213> ORGANISM: Artificial sequence
<220> FEATURE:
<223> OTHER INFORMATION: primer

<400> SEQUENCE: 2
caacctaata aaaaactata caaacacat                                     29

<210> SEQ ID NO 3
<211> LENGTH: 26
<212> TYPE: DNA
<213> ORGANISM: Artificial sequence
<220> FEATURE:
<223> OTHER INFORMATION: primer

<400> SEQUENCE: 3
ataagtatgt ttaattattg tttaag                                        26

<210> SEQ ID NO 4
<211> LENGTH: 32
<212> TYPE: DNA
<213> ORGANISM: Artificial sequence
<220> FEATURE:
<223> OTHER INFORMATION: primer

<400> SEQUENCE: 4
ggaatagttt agttaaagaa aaaggttaag at                                 32

<210> SEQ ID NO 5
<211> LENGTH: 34
<212> TYPE: DNA
<213> ORGANISM: Artificial sequence
<220> FEATURE:
<223> OTHER INFORMATION: primer

<400> SEQUENCE: 5
aatttaccac aatacacaaa aaactaacta ctta                               34

<210> SEQ ID NO 6
<211> LENGTH: 25
<212> TYPE: DNA
<213> ORGANISM: Artificial sequence
<220> FEATURE:
<223> OTHER INFORMATION: primer

<400> SEQUENCE: 6 agatttagt agtttttgt cgtta                                           25
```